United States Patent
Deboer et al.

[11] Patent Number: 6,123,684
[45] Date of Patent: Sep. 26, 2000

[54] LOADING MECHANISM FOR MEDICAL INJECTOR ASSEMBLY

[75] Inventors: David M. Deboer, Brighton, Mich.; Paul R. Lesch, Jr., Lexington; Sheldon J. Nelson, Plymouth, both of Minn.

[73] Assignee: Medi-Ject Corporation, Minneapolis, Minn.

[21] Appl. No.: 09/359,791

[22] Filed: Jul. 26, 1999

Related U.S. Application Data

[60] Provisional application No. 60/094,163, Jul. 27, 1998.

[51] Int. Cl.[7] .................................................. A61M 5/00
[52] U.S. Cl. .............................................. 604/68; 604/134
[58] Field of Search .............................. 604/68, 70, 71, 604/72, 134, 135, 187

[56] References Cited

U.S. PATENT DOCUMENTS

| | | |
|---|---|---|
| 2,322,244 | 6/1943 | Lockhart . |
| 2,322,245 | 6/1943 | Lockhart . |
| 2,380,534 | 7/1945 | Lockhart . |
| 2,398,544 | 4/1946 | Lockhart . |
| 2,450,527 | 10/1948 | Smith et al. . |
| 2,547,099 | 4/1951 | Smoot . |
| 2,635,601 | 4/1953 | May . |
| 2,645,223 | 7/1953 | Lawshe et al. . |
| 2,653,602 | 9/1953 | Smoot . |
| 2,785,678 | 3/1957 | Hein, Jr. . |
| 2,896,977 | 7/1959 | Hansen . |
| 3,066,670 | 12/1962 | Stauffer . |
| 3,145,712 | 8/1964 | Litz, Jr. . |
| 3,292,621 | 12/1966 | Banker . |
| 3,292,622 | 12/1966 | Banker . |
| 3,343,798 | 9/1967 | Senft . |
| 3,406,684 | 10/1968 | Tsujino . |
| 3,507,276 | 4/1970 | Burgess . |
| 3,518,990 | 7/1970 | Banker . |
| 3,540,444 | 11/1970 | Moreland . |
| 3,783,895 | 1/1974 | Weichselbaum . |
| 4,059,107 | 11/1977 | Iriguchi et al. . |
| 4,089,334 | 5/1978 | Schwebel et al. . |
| 4,103,684 | 8/1978 | Ismach . |
| 4,128,098 | 12/1978 | Bloom et al. . |
| 4,260,180 | 4/1981 | Halushka et al. . |
| 4,328,802 | 5/1982 | Curley et al. . |
| 4,338,980 | 7/1982 | Schwebel et al. . |
| 4,400,171 | 8/1983 | Dettbarn et al. . |
| 4,432,755 | 2/1984 | Pearson . |
| 4,447,225 | 5/1984 | Taff et al. . |
| 4,507,113 | 3/1985 | Dunlap . |
| 4,568,346 | 2/1986 | van Dijk . |
| 4,596,556 | 6/1986 | Morror et al. . |

(List continued on next page.)

FOREIGN PATENT DOCUMENTS

| | | |
|---|---|---|
| 2028870 | 10/1990 | Canada . |
| 959397 | 6/1964 | United Kingdom . |
| WO95/03844 | 7/1994 | WIPO . |
| WO9619252 | 12/1995 | WIPO . |
| WO9713537 | 9/1996 | WIPO . |
| WO97/22375 | 12/1996 | WIPO . |
| WO97/36785 | 3/1997 | WIPO . |

*Primary Examiner*—John D. Yasko
*Attorney, Agent, or Firm*—Pennie & Edmonds LLP

[57] ABSTRACT

A loading mechanism for a medical injector assembly is disclosed. The loading mechanism according to the present invention includes a dosing sleeve slidingly joining first and second injector housing portions and having tabs at a first end and fixed to one of the first or second housing portions at a second end; and a sleeve retainer fixed to the other of the first or second housing portions and engageable with the tabs of the dosing sleeve at an engagement point to prevent movement of the dosing sleeve once an injector plunger is at a rear portion of an injector fluid chamber, wherein movement of the first housing portion away from the second housing portion moves the plunger in a second direction to load fluid into the fluid chamber and movement of the first housing portion toward the second housing portion moves the plunger in a first direction to remove the fluid from the fluid chamber. The disclosed loading mechanism facilitates filling the assembly with medicament and priming the assembly for use.

12 Claims, 3 Drawing Sheets

U.S. PATENT DOCUMENTS

| | | |
|---|---|---|
| 4,616,856 | 10/1986 | Kowalyshen . |
| 4,623,332 | 11/1986 | Lindmayer et al. ............ 604/68 |
| 4,768,568 | 9/1988 | Fournier et al. . |
| 4,790,824 | 12/1988 | Morrow et al. . |
| 4,913,699 | 4/1990 | Parsons . |
| 5,024,656 | 6/1991 | Gasaway et al. . |
| 5,049,125 | 9/1991 | Accaries et al. . |
| 5,052,725 | 10/1991 | Meyer et al. . |
| 5,073,165 | 12/1991 | Edwards . |
| 5,112,317 | 5/1992 | Michel . |
| 5,176,406 | 1/1993 | Straghan . |
| 5,190,224 | 3/1993 | Hamilton . |
| 5,222,948 | 6/1993 | Austin et al. . |
| 5,360,413 | 11/1994 | Leason et al. . |
| 5,383,851 | 1/1995 | McKinnon, Jr. et al. . |
| 5,399,163 | 3/1995 | Peterson et al. . |
| 5,407,431 | 4/1995 | Botich et al. . |
| 5,425,465 | 6/1995 | Healy . |
| 5,429,256 | 7/1995 | Kestenbaum . |
| 5,454,409 | 10/1995 | McAffer et al. . |
| 5,454,805 | 10/1995 | Brony . |
| 5,470,319 | 11/1995 | Mayer . |
| 5,480,381 | 1/1996 | Weston . |
| 5,501,666 | 3/1996 | Spielberg . |
| 5,520,639 | 5/1996 | Peterson et al. . |
| 5,569,189 | 10/1996 | Parsons . |
| 5,573,516 | 11/1996 | Tyner . |
| 5,599,302 | 2/1997 | Lilley et al. ............ 604/68 |
| 5,704,911 | 1/1998 | Parsons . |
| 5,769,138 | 6/1998 | Sadowski et al. . |
| 5,879,327 | 3/1999 | DeFarges et al. ............ 604/68 |
| 5,891,086 | 4/1999 | Weston ............ 604/70 |

LOADING MECHANISM FOR MEDICAL INJECTOR ASSEMBLY

This is a provision of 60/094,163 filed Jul. 27, 1998.

FIELD OF THE INVENTION

The present invention is directed to medical injectors, and in particular to a loading mechanism for filling a medical injector assembly with medicament.

BACKGROUND OF THE INVENTION

Needleless injectors, such as those described in U.S. Pat. No. 5,599,302 issued to Lilley et al., U.S. Pat. No. 5,062,830 to Dunlap, and U.S. Pat. No. 4,790,824 to Morrow et al., must eject medicament at a pressure ($P_{piercing}$) that is sufficient to pierce the skin so that the medicament can be delivered to the desired area, usually the subcutaneous region. Ordinarily, $P_{piercing}$ is approximately 4000 psi. The need to achieve such a high pressure has imposed certain design limitations that affect many of the operational aspects of needleless injectors. One such aspect is the manner in which needleless injectors are filled with medicament.

For conventional needle-containing syringes, filling the syringe with medicament requires only simple "pull-push" motions. Specifically, the plunger of the syringe is pulled back with the needle inserted in the medicament vial to fill the syringe with the desired amount of medicament. After the needle is removed from the vial, the plunger is pushed forward to prime the syringe, i.e., remove any air bubbles. In contrast, filling needleless injectors with medicament is a laborious and lengthy multi-step procedure. For example, with the Medi-Jector Choice™ injector available from Medi-Ject Corporation of Minneapolis, Minn., the body of the injector is repeatedly twisted in a first direction to ready the injector for medicament delivery. Next, the user attaches the nozzle of the injector to the medicament vial and repeatedly twists the body in a second direction until the desired amount of medicament is drawn into the nozzle chamber. Finally, the user twists the body in the first direction to prime the injector, i.e., remove any air bubbles from the nozzle chamber. As the Medi-Jector Choice™ injector, like any conventional needleless injector, uses a high force energy mechanism (i.e., a coil spring), twisting the body of the injector can be difficult.

Advances in needleless injector technology have made the use of lower force energy mechanisms feasible. The use of lower force energy mechanisms has reduced the design constraints on needleless injectors. Lower force energy mechanisms would also be useful in intradermal applications such as vaccine, specifically DNA vaccines in which a high force energy mechanism could disrupt the molecular structure. Such use is disclosed in "Intradermal DNA Immunization by Using Jet-Injectors in Mice and Monkeys," Vaccine, 17:628–38, February 1999.

Thus, for both high force and low force injectors, there still exists a need for a needleless injector using an improved loading mechanism to fill the injector with medicament.

SUMMARY OF THE INVENTION

An injection device having a loading mechanism according to the present invention has a first housing portion, a second housing portion slidingly connected with the first housing portion, a nozzle assembly defining a fluid chamber, a plunger movable within the fluid chamber between a first position in a proximal portion of the chamber and a second position in a distal portion of the chamber, a trigger assembly, and an energy generating source operatively associated with the trigger assembly so that movement of the trigger assembly activates the energy source to move the plunger toward the proximal portion and expel fluid from the fluid chamber. The loading mechanism comprises a dosing sleeve slidingly joining the first and second housing portions, and having tabs at a first end and fixed to one of the first or second housing portions at a second end; and a sleeve retainer fixed to the other of the first or second housing portions and engageable with the tabs of the dosing sleeve at an engagement point to prevent movement of the dosing sleeve once the plunger is moved to the second position of the fluid chamber. Movement of the first housing portion away from the second housing portion moves the plunger toward the distal portion to load fluid into the fluid chamber and movement of the first housing portion toward the second housing portion moves the plunger toward the proximal portion to remove fluid from the fluid chamber.

The injection device can either be a low force injector, operating at a pressure less than about 4000 psi, or a high force injector, operating at a pressure that is greater than about 4000 psi.

In one embodiment, the nozzle assembly is removably associated with the first housing portion. The energy generating source preferably includes a coil spring. The coil spring can be located within the dosing sleeve. In order to vary the fluid quantity loaded into the fluid chamber, the sleeve retainer can include an adjustable ring to change the engagement point.

Preferably, the dosing sleeve is fixed to the second housing portion and the sleeve retainer is fixed to the first housing portion. The injection device can also include a screw for securing the sleeve retainer to the first housing portion, a threaded hole in the first housing portion, and a threaded hole in the sleeve retainer. The first housing portion threaded hole aligns with the sleeve retainer threaded hole to threadably receive the screw.

A ram preferably extends from the plunger and is located within the dosing sleeve. The ram can include an inertia mass on a first end which cooperates with a ram retainer located within the first housing portion to prevent ejection of the ram from the first housing portion.

DESCRIPTION OF THE PREFERRED EMBODIMENTS

Figure 1:
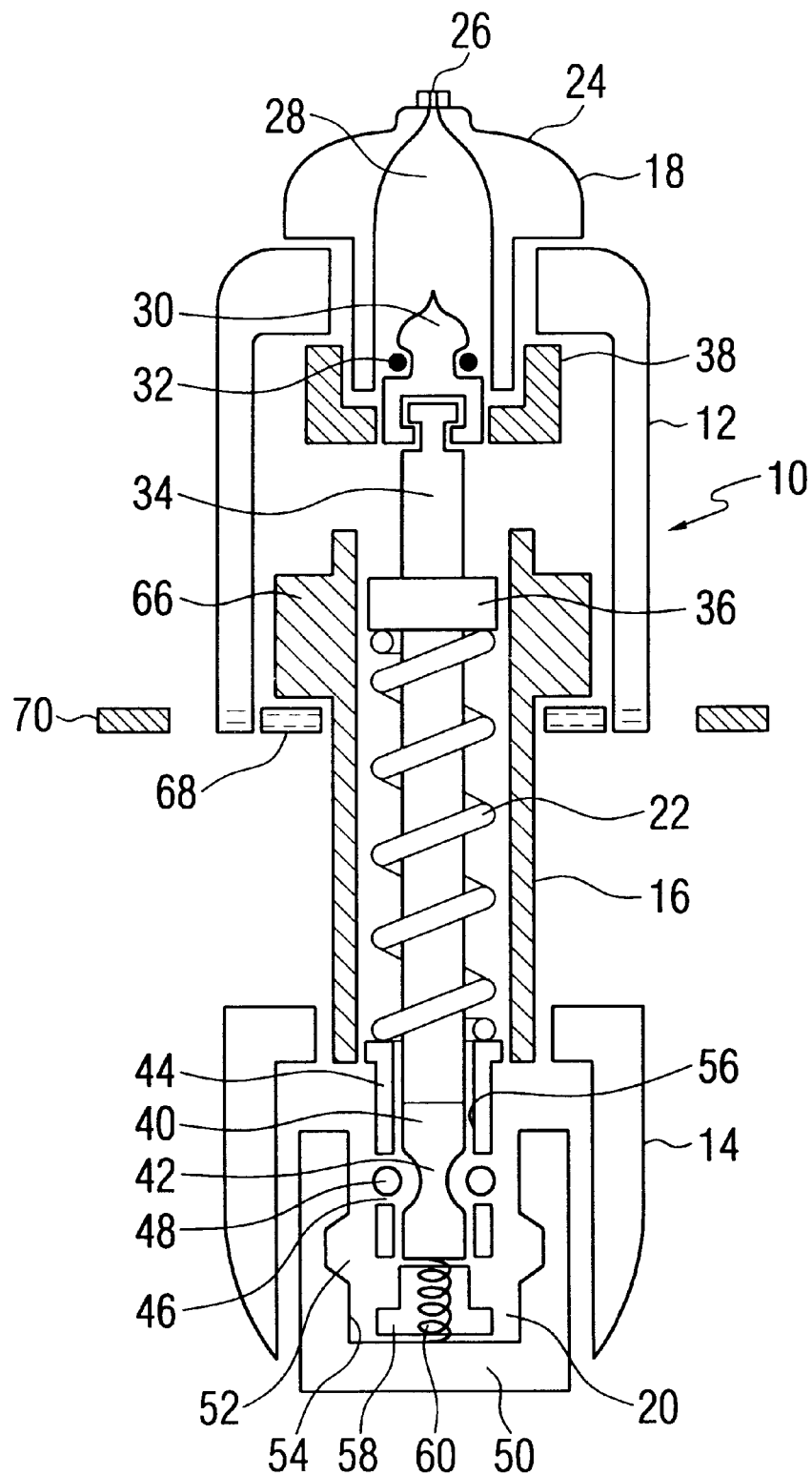
FIG. 1 is a cross sectional view of a needleless injector with a loading mechanism according to the present invention with the injector in the latched position.
Figure 2:
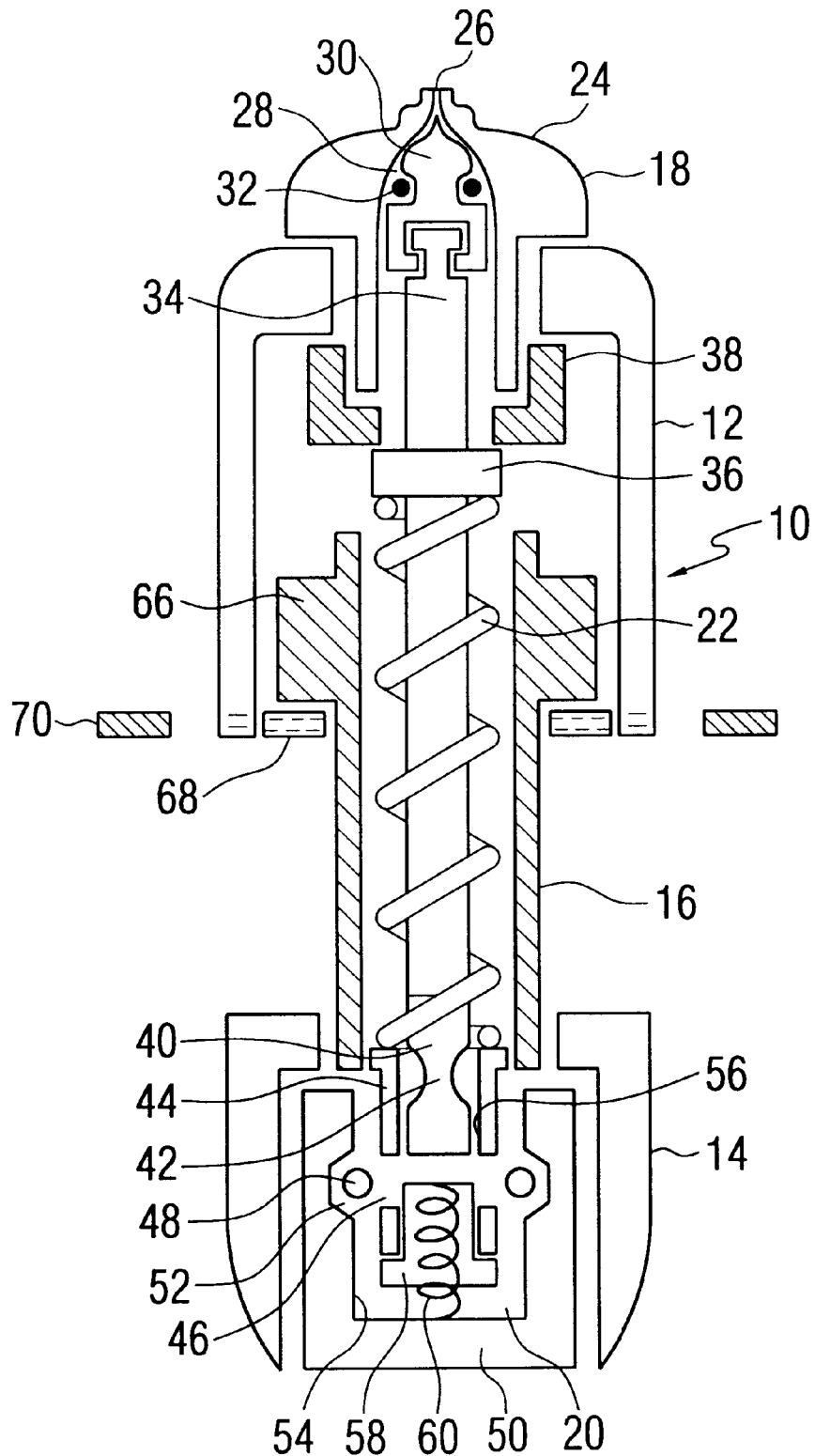
FIG. 2 is a cross sectional view of the needleless injector with the loading mechanism according to the present invention with the injector in the unlatched position.

As shown in FIGS. 1 and 2, a needleless injector 10 comprises a first housing portion 12, a second housing portion 14, and a dosage sleeve 16 joining first and second housing portion 12 and 14. A nozzle assembly 18 is attached to an end of first housing portion 12. Nozzle assembly 18 can be threadably connected to first housing portion 12 such that it can be readily attached and detached. Alternatively, other known structures for mounting or attaching two components can be utilized as well to detachably mate nozzle assembly 18 to first housing portion 12. In this manner, needleless injector 10 can be reused with various nozzle assemblies. One advantage of this configuration is that needleless injector 10 can be used with disposable nozzle assemblies. A trigger assembly 20 is located on second housing portion 14. Trigger assembly 20 activates and triggers an energy source 22 which forces medicament out of nozzle assembly 18. Although energy source 22 is shown as a coil spring, other force generating means, such as a gas spring or a gas propellant, can be used for energy source 22.

Nozzle assembly 18 includes a nozzle member 24 having an orifice 26 of a suitable diameter that would produce a jet stream of medicament under a given desired pressure range and depth of injection. Orifice 26 can be any type of opening, including a straight, convergent, divergent, convergent-divergent, etc. Nozzle assembly 18 also has a cylindrical chamber 28 terminating in a cone leading to orifice 26. As described in more detail below, medicament is loaded into and ejected from chamber 28 in use of injector 10. The cone can be a convex cone (as shown), a right circular cone, or any other suitable configuration. A plunger 30 having a pressure wall contoured to the cone of chamber 28 is positioned to slide within chamber 28. Plunger 30 can include a sealing means 32 such as an O-ring(s) or the like formed around its outer periphery to provide a seal or the plunger itself can be a seal, as described, for instance in U.S. Pat. No. 5,062,830 patent, the disclosure of which is incorporated herein by reference. Plunger 30 can also include additional sealing means at spaced intervals to provide a better seal.

Plunger 30 is connected to a ram 34 which in turn is connected to energy source 22. Alternatively, ram 34 can be integrally formed with an energy mechanism if desired. An inertia mass 36 is connected to or integrally formed with ram 34 near the end of ram 34 closest to plunger 30. Inertia mass 36 can be removably connected to ram 34 such that the mass can be adjusted to accommodate different types of injections, taking into consideration, for instance, the viscosity of the medication, the initial pressure build up desired, the strength of energy source 22, and the depth of injection penetration, etc. Inertia mass 36 cooperates with ram retainer 38 to limit the distance that ram 34 can travel toward nozzle assembly 18. One important safety aspect of this feature is that ram 34 cannot become a dangerous projectile if injector 10 is fired when nozzle assembly 18 is not present.

Trigger assembly 20 includes a trigger extension 40 having a trigger engaging notch 42. Trigger extension 40 is attached to the end of ram 34, for example, by a threaded engagement. Trigger assembly 20 also comprises a latch housing sleeve 44 fixedly attached to dosage sleeve 16. Latch housing sleeve 44 has a throughbore dimensioned to allow passage of trigger extension 40. Latch housing sleeve 44 further has a plurality of sidewall openings 46 dimensioned to allow passage of balls or ball bearings 48. A tubular button 50 having one open end and a closed end is telescopingly positioned with latch housing sleeve 44 as shown. Button 50 has a circumferential or annular groove 52 formed on an inner wall 54 thereof to allow portions of the balls 48 to engage groove 52 when trigger assembly 20 is in the fired position as shown in FIG. 2 (not engaged with trigger extension 40). Balls 48 are positioned so that they are substantially flush with an inner side wall surface 56 of latch housing sleeve 44 as also shown in FIG. 2 to allow trigger extension 40 to pass through latch housing sleeve 44. A latch ball retaining cup 58 is telescopingly positioned within button 50. A compression spring 60 is positioned between the cup 58 and button 50 to bias button 50 and cup 58 away from each other in the axial direction.

Figure 3A:
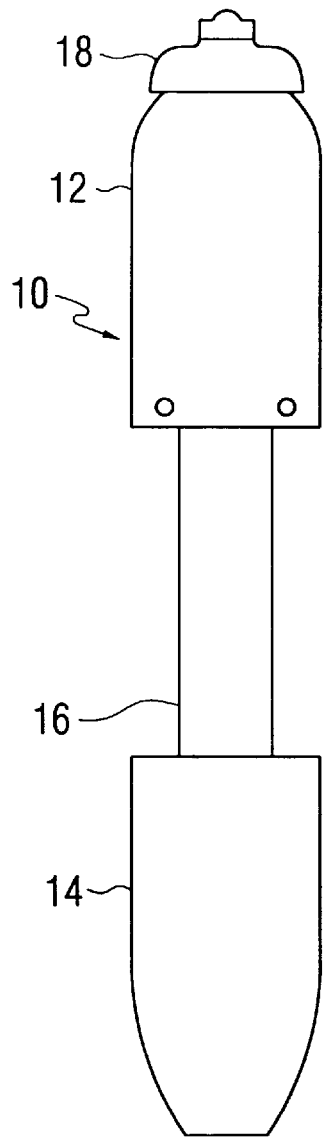
FIG. 3A is a side view showing the needleless injector with the loading mechanism according to the present invention with the injector in the unlatched position.
Figure 3B:
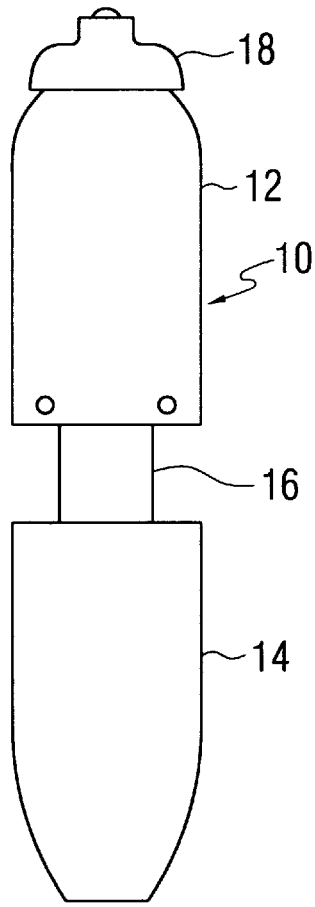
FIG. 3B is a side view showing the needleless injector with the loading mechanism according to the present invention with the injector in the latched position.

FIGS. 2 and 3A show injector 10 in a unarmed or unlatched position, i.e., in the state in which first and second housing portions 12 and 14 are not operatively associated with each other so that activation of an energy source 22 forces medicament out of nozzle assembly 18. FIGS. 1 and 3B show injector 10 in an armed or latched position, i.e., in the state in which first and second housing portions 12 and 14 are operatively associated with each other so that activation of energy source 22 forces medicament out of nozzle assembly 18.

Injector 10 is brought from the unlatched position of FIGS. 2 and 3A to the latched position of FIGS. 1 and 3B by simply moving first and second housing portions 12 and 14 closer together. Specifically, as second housing portion 12 moves toward trigger extension 40, latch retaining cup 58 is pushed outwardly, causing balls 48 to engage trigger engaging notch 42 formed on trigger extension 40. Compression spring 60 forces button 50 outwardly. Balls 48 are locked in the position between notch 42 and inner side wall 54 of button 50, locking ram 34 to trigger assembly 20. When trigger extension 40 is locked to latch housing sleeve 44, moving first housing portion 12 closer to second housing portion 14 further compresses energy source 22.

Figure 3C:
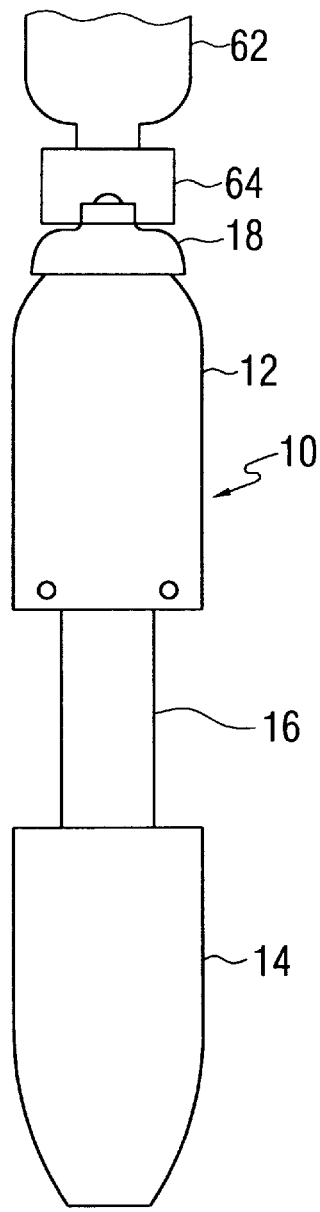
FIG. 3C is a side view showing the needleless injector with the loading mechanism according to the present invention with the injector connected to a medicament vial.

Although trigger extension 40 is locked to latch housing sleeve 44, first housing portion 12 is free to slide along the length of dosing sleeve 16. As first housing portion 12 moves along dosing sleeve 16, plunger 30 moves relative to cylindrical chamber 28. If nozzle assembly 18 is connected to a medicament-containing vial 62 when injector 10 is in the latched position as shown in FIG. 3C, then movement of plunger 30 in the direction toward second housing portion 14 draws the medicament into chamber 28. FIG. 3C shows nozzle assembly 18 connected to vial 62 via a coupling device 64. Any design that mates with nozzle assembly 18 can be used for coupling device 64. For example, the coupling devices disclosed in U.S. Pat. No. 5,599,302 to Lilley et al.; U.S. Pat. No. 5,769,138 to Sadowski et al.; and U.S. Pat. No. 4,507,113 to Dunlap, the contents of which are incorporated herein by reference, are examples of acceptable designs. In order to purge any air bubbles from chamber 28, second housing portion 14 is moved toward first housing portion 12. This can be done either before or after disconnecting coupling device 64 from nozzle assembly 18.

Tabs 66 are located on the end of dosing sleeve 16 closest to first housing portion 12. Tabs 66 cooperate with sleeve retainer 68 to prevent first housing portion 12 from sliding completely off of dosing sleeve 16. Set screws 70 attach sleeve retainer to first housing portion 12. As tabs 66 and sleeve retainer 68 limit the amount of movement of plunger 30 with respect to chamber 28, tabs 66 and sleeve retainer 68 also limit the amount of medicament that enters chamber 28. Thus, if sleeve retainer 68 is an adjustable ring such that the amount of travel of second housing portion 14 on dosage sleeve 16 is adjustable, variable doses of medicament can be metered.

If injector 10 uses a high force energy mechanism, then people possessing average strength should be able to overcome the energy mechanism and push first housing portion 12 closer to second housing portion 14. For people having minimal strength, an arming station comprising two surfaces spaced apart to receive unlatched injector 10 and movable under the power of a motor can be used to latch injector 10. If injector 10 uses a low force energy mechanism, even those of minimal strength should be able to push first housing portion 12 closer to second housing portion 14.

While it is apparent that the illustrative embodiments of the invention herein disclosed fulfil the objectives stated above, it will be appreciated that numerous modifications and other embodiments may be devised by those skilled in the art. Therefore, it will be understood that the appended claims are intended to cover all such modifications and embodiments which come within the spirit and scope of the present invention.

What is claimed is:

1. An injection device having a loading mechanism, wherein said injection device has a first housing portion, a second housing portion slidingly connected with the first housing portion, a nozzle assembly defining a fluid chamber, a plunger movable within the fluid chamber between a first position in a proximal portion of the chamber and a second position in a distal portion of the chamber, a trigger assembly, and an energy generating source operatively associated with the trigger assembly so that movement of the trigger assembly activates the energy source to move the plunger toward the proximal portion and expel fluid from the fluid chamber, said loading mechanism comprising:

a dosing sleeve slidingly joining the first and second housing portions, said dosing sleeve having tabs at a first end and fixed to one of the first or second housing portions at a second end; and a sleeve retainer fixed to the other of the first or second housing portions and engageable with the tabs of the dosing sleeve at an engagement point to prevent movement of the dosing sleeve once the plunger is moved to the second position of the fluid chamber, wherein movement of the first housing portion away from the second housing portion moves the plunger toward the distal portion to load fluid into the fluid chamber and movement of the first housing portion toward the second housing portion moves the plunger toward the proximal portion to remove fluid from the fluid chamber.

2. The injection device of claim 1 wherein the nozzle assembly is removably associated with the first housing portion.

3. The injection device of claim 1 wherein the energy generating source includes a coil spring.

4. The injection device of claim 3 wherein the coil spring is located within the dosing sleeve.

5. The injection device of claim 1 wherein the sleeve retainer includes an adjustable ring to change the engagement point and thereby vary the fluid quantity loaded into the fluid chamber.

6. The injection device of claim 1 wherein the dosing sleeve is fixed to the second housing portion and the sleeve retainer is fixed to the first housing portion.

7. The injection device of claim 6 further comprising a screw for securing the sleeve retainer to the first housing portion, a threaded hole in the first housing portion, and a threaded hole in the sleeve retainer, the first housing portion threaded hole aligning with the sleeve retainer threaded hole to threadably receive the screw.

8. The injection device of claim 1 wherein a ram extends from the plunger and is located within the dosing sleeve.

9. The injection device of claim 1 wherein the ram includes an inertia mass on a first end.

10. The injection device of claim 1 further comprising a ram retainer located within the first housing portion for preventing ejection of the ram from the first housing portion.

11. The injection device of claim 1 wherein the injection device operates at a pressure that is less than about 4000 psi.

12. The injection device of claim 1 wherein the injection device operates at a pressure that is greater than about 4000 psi.

* * * * *